(12) United States Patent
Nie et al.

(10) Patent No.: US 12,144,560 B2
(45) Date of Patent: Nov. 19, 2024

(54) OPTICAL SCALE AND METHOD FOR COORDINATE SYSTEM REGISTRATION

(71) Applicant: BOE TECHNOLOGY GROUP CO., LTD., Beijing (CN)

(72) Inventors: Liping Nie, Beijing (CN); Hao Wang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 651 days.

(21) Appl. No.: 17/418,358

(22) PCT Filed: Dec. 29, 2020

(86) PCT No.: PCT/CN2020/140896
§ 371 (c)(1),
(2) Date: Jun. 25, 2021

(87) PCT Pub. No.: WO2021/184911
PCT Pub. Date: Sep. 23, 2021

(65) Prior Publication Data
US 2022/0304751 A1 Sep. 29, 2022

(30) Foreign Application Priority Data
Mar. 17, 2020 (CN) .......................... 202010189269.4

(51) Int. Cl.
*A61B 34/20* (2016.01)
*A61B 34/32* (2016.01)
(Continued)

(52) U.S. Cl.
CPC .............. *A61B 34/20* (2016.02); *A61B 34/32* (2016.02); *G06T 7/11* (2017.01); *G06T 7/30* (2017.01);
(Continued)

(58) Field of Classification Search
CPC . A61B 34/20; A61B 34/32; A61B 2034/2055; A61B 2034/2065;
(Continued)

(56) References Cited

U.S. PATENT DOCUMENTS

2005/0259874 A1  11/2005  Sano et al.
2009/0046908 A1*  2/2009  Safdar .................... A61B 5/055
                                                    382/128
(Continued)

FOREIGN PATENT DOCUMENTS

CN        1699917 A    11/2005
CN     101394791 A     3/2009
(Continued)

OTHER PUBLICATIONS

China Patent Office, First Office Action dated Nov. 23, 2020, for corresponding Chinese application No. 202010189269.4.
(Continued)

*Primary Examiner* — Mia M Thomas
(74) *Attorney, Agent, or Firm* — HOUTTEMAN LAW LLC

(57) ABSTRACT

The embodiment of the present disclosure provides an optical scale comprising a support and at least three markers, wherein, the markers are fixed on the support; among all the markers, there are at least three markers whose geometric centers are not collinear; any two of the markers are different in at least one of size and shape, and any different markers do not contact each other; the material of the marker and the support enables that in a three-dimensional image obtained by three-dimensional imaging technology, the difference between a gray scale of the marker and a gray scale of the support exceeds a first predetermined value. The embodiment of the present disclosure provides a method for coordinate system registration. The embodiment of the present disclosure further provides a method for coordinate system registration by using the above optical scale.

13 Claims, 5 Drawing Sheets

(51) Int. Cl.
  *A61B 90/00* (2016.01)
  *G06T 7/11* (2017.01)
  *G06T 7/30* (2017.01)
  *G06T 7/60* (2017.01)
  *G06T 7/70* (2017.01)
(52) U.S. Cl.
  CPC .................. *G06T 7/60* (2013.01); *G06T 7/70* (2017.01); *A61B 2034/2055* (2016.02); *A61B 2034/2065* (2016.02); *A61B 2090/3762* (2016.02); *A61B 2090/3937* (2016.02); *G06T 2200/04* (2013.01); *G06T 2207/10012* (2013.01); *G06T 2207/10081* (2013.01); *G06T 2207/30204* (2013.01)
(58) Field of Classification Search
  CPC .... A61B 2090/3762; A61B 2090/3937; A61B 2034/2068; A61B 90/39; A61B 2090/3966; A61B 2090/3983; G06T 7/11; G06T 7/30; G06T 7/60; G06T 7/70; G06T 2200/04; G06T 2207/10012; G06T 2207/10081; G06T 2207/30204; G06T 7/62
  See application file for complete search history.

(56) References Cited

U.S. PATENT DOCUMENTS

| | | | |
|---|---|---|---|
| 2009/0310832 A1 | 12/2009 | Kim | |
| 2013/0331850 A1* | 12/2013 | Bojarski | A61F 2/4657 606/102 |
| 2014/0002642 A1* | 1/2014 | Swiegot | G06T 7/60 348/137 |
| 2014/0073907 A1* | 3/2014 | Kumar | A61B 10/0241 600/407 |
| 2014/0276002 A1* | 9/2014 | West | G06T 19/00 600/424 |
| 2017/0303849 A1* | 10/2017 | De Sapio | A61B 5/4023 |
| 2017/0340389 A1* | 11/2017 | Otto | A61B 34/10 |
| 2017/0360513 A1* | 12/2017 | Amiot | A61B 34/20 |
| 2019/0142359 A1 | 5/2019 | Zhang et al. | |
| 2020/0261297 A1* | 8/2020 | Strydom | G06T 7/60 |
| 2021/0212772 A1* | 7/2021 | Yang | A61B 90/30 |

FOREIGN PATENT DOCUMENTS

| | | |
|---|---|---|
| CN | 202288472 U | 7/2012 |
| CN | 103040471 A | 4/2013 |
| CN | 103325143 A | 9/2013 |
| CN | 104083216 A | 10/2014 |
| CN | 104504760 A | 4/2015 |
| CN | 107468350 A | 12/2017 |
| CN | 107708568 A | 2/2018 |
| CN | 109363770 A | 2/2019 |
| CN | 111388091 A | 7/2020 |
| DE | 202007004166 U1 | 8/2007 |
| WO | WO2017003453 A1 | 1/2017 |

OTHER PUBLICATIONS

China Patent Office, Second Office Action dated Jun. 10, 2021, for corresponding Chinese application No. 202010189269.4.
China Patent Office, Third Office Action dated Dec. 3, 2021, for corresponding Chinese application No. 202010189269.4.

* cited by examiner

OPTICAL SCALE AND METHOD FOR COORDINATE SYSTEM REGISTRATION

CROSS REFERENCE TO RELATED APPLICATION

This application is a National Phase Application filed under 35 U.S.C. 371 as a national stage of PCT/CN2020/140896, filed on Dec. 29, 2020, an application claiming the priority of the Chinese patent application No. 202010189269.4, filed on Mar. 17, 2020, the contents of which are incorporated herein by reference in their entirety.

TECHNICAL FIELD

The present disclosure relates to the technical field of automatic surgery, and particularly relates to an optical scale and a method for coordinate system registration.

BACKGROUND

The automated surgery (navigated surgery) means that a surgical robot automatically performs a desired surgical operation (for example, drilling a hole in a specific position of a specific vertebra) on a patient according to a preset surgical plan. The automated surgery has the advantages of precise operation, no mistakes, low possibility of infection, no labor consumption, high efficiency, and etc.

The procedure of the automated surgery usually comprises obtaining a three-dimensional image of a patient by three-dimensional imaging technology, marking a surgical plan in the three-dimensional image by a doctor, and automatically performing a surgical robot on the patient according to the surgical plan.

Since the surgical robot and the three-dimensional image (or the three-dimensional imaging system) have their respective coordinate systems, it is necessary to register the coordinate systems of the two systems (or determine the relative position relationship between the two coordinate systems), such that the surgical robot is enabled to determine the position of the surgical robot relative to the three-dimensional image (that is, the position of the surgical robot relative to the patient), so as to perform the surgery on the accurate part of the patient body.

However, the prior art cannot accurately and quickly realize coordinate system registration.

SUMMARY

The embodiment of the present disclosure provides an optical scale and a method for coordinate system registration.

In a first aspect, the embodiment of the present disclosure provides an optical scale comprising a support and at least three markers, wherein,
  the markers are fixed on the support; among all the markers, there are at least three markers whose geometric centers are not collinear; any two of the markers are different in at least one of size and shape, and any different markers do not contact each other;
  the material of the marker and the support enables that in a three-dimensional image obtained by three-dimensional imaging technology, the difference between a gray scale of the marker and a gray scale of the support exceeds a first predetermined value.

In some embodiments, all of the markers have the same shape, and any two of the markers have different sizes.

In some embodiments, all of the markers are spherical, and any two of the markers have different diameters.

In some embodiments, there are at most two geometric centers of the markers in any one line.

In some embodiments, the geometric centers of all of the markers are located in the same plane.

In some embodiments, the support is a flat plate, and all the markers are embedded in the flat plate.

In some embodiments, the optical scale further comprising:
  a connecting structure connected to the support and is used for fixing the support on a surgical robot.

In some embodiments, the material of the marker enables that in a three-dimensional image obtained by three-dimensional imaging technology, the difference between a gray scale of the marker and a gray scale of human body exceeds a second predetermined value.

In some embodiments, the marker is made of steel;
the support is made of plastic.

In a second aspect, the embodiment of the present disclosure provides a method of coordinate system registration, comprising:
  fixing an optical scale on a determined position of a surgical robot, wherein the optical scale is the any one of the above optical scales;
  obtaining a three-dimensional image comprising the optical scale by three-dimensional imaging technology;
  determining the position of the geometric center of each marker of the optical scale in the three-dimensional image.
  registering the coordinate system of the surgical robot and the coordinate system of the three-dimensional image according to the position of the optical scale relative to the surgical robot and the position of the geometric center of each marker of the optical scale in the three-dimensional image.

In some embodiments, the three-dimensional imaging technology is a CT imaging technology.

In some embodiments, the step that obtaining the three-dimensional image comprising the optical scale by three-dimensional imaging technology comprising:
  obtaining a plurality of tomographic images by CT imaging technology;
  reconstructing to obtain a three-dimensional image comprising the optical scale according to the plurality of tomographic images.

In some embodiments, the step that determining the position of the geometric center of each marker of the optical scale in the three-dimensional image comprising:
  performing image segmentation on the three-dimensional image based on the shape and/or size of the marker to obtain a plurality of segmented regions;
  filtering each of the segmented regions based on the gray scale of the marker, and only keeping the marking points corresponding to the marker;
  extracting a plurality of characteristic regions based on the shape and/or size of the marker, wherein each characteristic region comprises all the marking points corresponding to one marker;
  determining the shape and/or size of the virtual marker formed by the marking points in each characteristic region, and the position of the geometric center of the virtual marker in the three-dimensional image according to the marking points in each characteristic region;
  determining a corresponding relationship between the virtual marker and the marker based on the size and/or shape of the marker, with the position of the geometric center of the virtual marker in the three-dimensional image as the position of the geometric center of the corresponding marker in the three-dimensional image.

In some embodiments, the step that performing image segmentation on the three-dimensional image based on the shape and/or size of the marker to obtain a plurality of segmented regions comprising:

performing image segmentation on the three-dimensional image through a Marching Cubes algorithm based on the shape and/or size of the marker.

In the optical scale according to the embodiment of the present disclosure, the shape and/or size of different markers are different, that is, the size and/or shape of different markers in the three-dimensional image are also different, so that by analyzing the size and shape of the marker in the three-dimensional image, the corresponding relationship between the marker in the three-dimensional image and the actual marker can be identified (or the markers can be identified), and the coordinate system registration between the surgical robot and the three-dimensional image (or three-dimensional imaging system) can be realized.

Therefore, the coordinate system registration of the embodiment of the present disclosure can be automatedally performed, so that it does not require manual intervention, and is simple to be operated, efficient and accurate. Moreover, in the embodiment of the present disclosure, by analyzing the shape and size of the marker in the three-dimensional image, the corresponding relationship between the marker in the three-dimensional image and the actual marker can be determined (or the marker can be identified), without the need to analyze the position relationship (arrangement) between the markers, such that the required calculation process is simple, the amount of calculation is small and the time consumption is short.

BRIEF DESCRIPTION OF THE DRAWINGS

The accompanying drawings are included to provide a further understanding of the embodiments of the disclosure, and are incorporated in and constitute a part of this specification, and together with the embodiments of the present disclosure serve to explain the principles of the disclosure, and are not limited herein. The above and other features and advantages will become more apparent to those skilled in the art by describing in detail exemplary embodiments thereof with reference to the attached drawings, in which.

Figure 1:
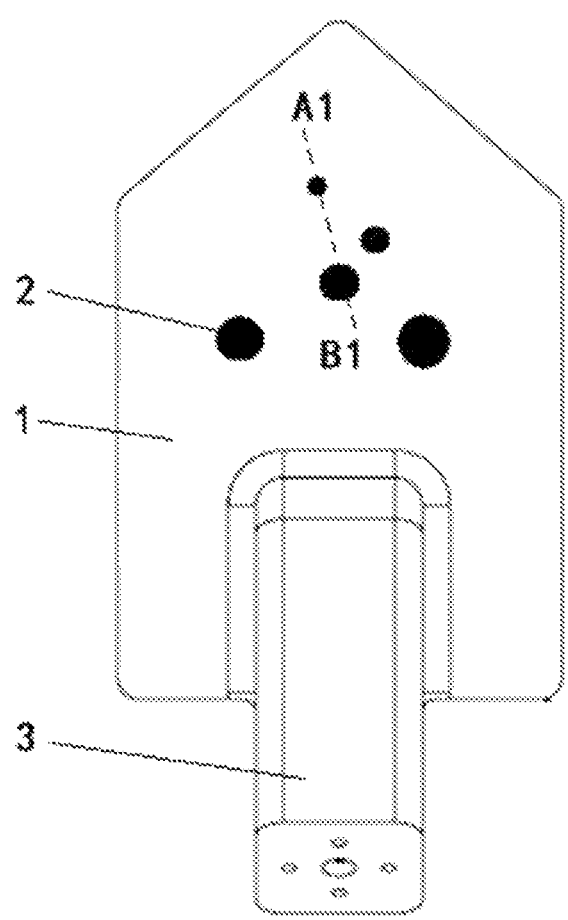
FIG. 1 is a schematic front view of an optical scale according to an embodiment of the present disclosure.

wherein the reference numbers are:
1. support; 11. opening; 2. marker; 3. connecting structure.

DETAILED DESCRIPTION OF THE EMBODIMENTS

To improve understanding of the technical solution of the embodiments of the present disclosure for those skilled in the of art, the optical scale and the method for coordinate system registration according to the embodiments of the present disclosure is described in detail below with reference to the accompanying drawings.

The embodiments of the present disclosure will be described more fully hereinafter with reference to the accompanying drawings, but the illustrated embodiments can be embodied in different forms, and should not be construed as limited to the embodiments set forth herein. Rather, the purpose of providing the embodiments is to make the present disclosure thorough and complete, and to enable those skilled in the art to fully understand the scope of the present disclosure.

The embodiments of the present disclosure can be described with reference to plan views and/or cross-sectional views by way of idealized schematic diagrams of the present disclosure. Accordingly, the example illustrations can be modified according to manufacturing techniques and/or tolerances.

In the absence of conflict, the various embodiments and features of the embodiments of the present disclosure can be combined with each other.

The terms used in the present disclosure are used only to describe particular embodiments and are not intended to limit the present disclosure. The term "and/or" as used in the present disclosure comprises any and all combinations of one or more of the related listed items. The singular forms "a", "an" and "the" as used in the present disclosure are also intended to include the plural forms, unless the context clearly indicates otherwise. The terms "comprises", "made of" as used in the present disclosure specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used in the present disclosure have the same meaning as commonly understood by one of ordinary skill in the art. It will be further understood that terms, such as those defined in commonly used dictionaries, should be interpreted as having meanings consistent with their meaning in the relevant art and in the background of the present disclosure, and will not be interpreted in an idealized or overly formal meaning unless expressly so defined herein.

The embodiments of the present disclosure are not limited to the embodiments shown in the drawings, but include modifications of configurations formed based on the manufacturing process. Thus, the regions illustrated in the drawings have schematic properties, and the shapes of the regions shown in the drawings illustrate specific shapes of regions of elements, but are not intended to be limiting.

In some related technologies, in the process of automated surgery, an optical scale can be installed at a specific position of a surgical robot before actually starting surgery, and the optical scale comprises a plurality of markers with the same shape and size, so that the markers will also be included in the resulting three-dimensional image; in this way, once the position of each marker in the three-dimensional image is determined, the relative positions of the coordinate systems of the surgical robot and the three-dimensional image (or the three-dimensional imaging system) can be determined by using the marker as the medium, so as to realize the coordinate system registration, so that the surgical robot performs the surgery according to the structure of the coordinate system registration.

In this case, the position of each marker in the three-dimensional image can be determined manually, that is, an operator (e.g., a doctor) marks the position of each marker in the three-dimensional image in sequence based on the experience of the doctor. However, such a method is inevitably affected by human factors (such as technical level, mistakes, etc.), and therefore, the position accuracy is difficult to be ensured, and manual intervention is required, so that the operation is complicated and the efficiency is low.

Alternatively, by the relative positions (arrangement) of the markers, the markers can be automatedally identified from the image and the positions of the markers can be automatedally determined. However, the calculation process in such a method is complicated, requiring a large amount of calculation, and takes a long time.

Figure 2:
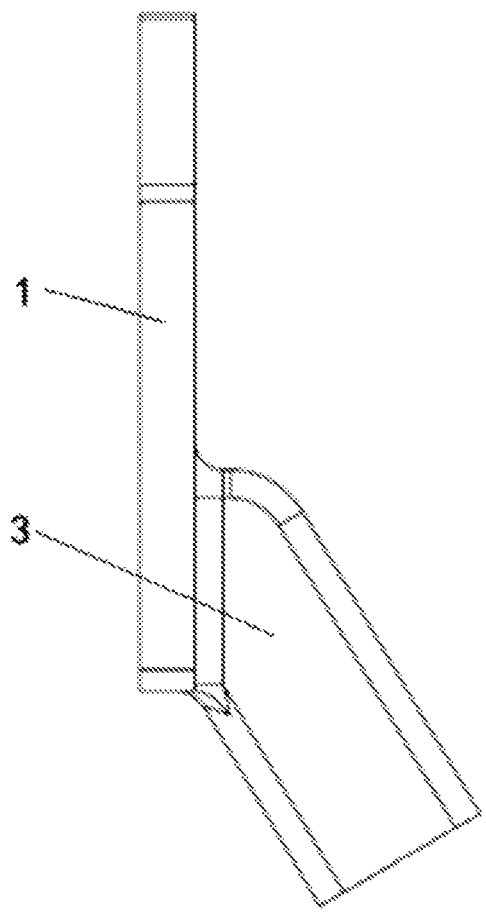
FIG. 2 is a schematic side view of an optical scale according to an embodiment of the present disclosure.
Figure 3:
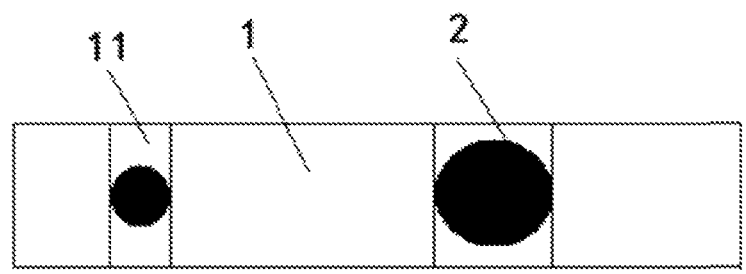
FIG. 3 is a schematic cross-sectional view taken along line A1B1 in FIG. 1.

In a first aspect, referring to FIGS. 1 to 3, an embodiment of the present disclosure provides an optical scale.

The optical scale of the embodiment of the present disclosure is used in the field of automated surgery.

Specifically, the optical scale can be installed at a determined position of a surgical robot before three-dimensional imaging, such that a three-dimensional image comprising at least the optical scale can be obtained by three-dimensional imaging technology. Of course, the three-dimensional view can also include at least a part of the surgical robot.

Since the optical scale is installed at a determined position of the surgical robot (e.g. at the head of the surgical robot), the position of the optical scale in the coordinate system of the surgical robot can be determined. Meanwhile, by the method of the embodiment of the present disclosure, the position of the optical scale in the three-dimensional image can be determined, that is, the position of the optical scale in the coordinate system of the three-dimensional image (or the three-dimensional imaging system) is also known.

Since the position of the optical scale in the real world is unique, the position of the optical scale in the coordinate system of the surgical robot and the position of the optical scale in the coordinate system of the three-dimensional image should be actually one position, and accordingly, the relative position relationship between the coordinate system of the surgical robot and the coordinate system of the three-dimensional image can be obtained, that is, the registration of the coordinate systems of the surgical robot and the three-dimensional image (three-dimensional imaging system) can be realized.

Specifically, the optical scale of the embodiment of the present disclosure comprises a support 1 and at least three markers 2, wherein the markers 2 are fixed on the support 1; among all the markers 2, there are at least three markers 2 whose geometric centers are not collinear; any two of the markers 2 are different in at least one of size and shape, and any different markers 2 do not contact each other.

Moreover, the material of the marker 2 and the support 1 enables that in a three-dimensional image obtained by three-dimensional imaging technology, the difference between the gray scale of the marker 2 and the gray scale of the support 1 in exceeds a first predetermined value.

Referring to FIGS. 1 and 2, the optical scale comprises a support 1 and a plurality of markers 2 fixed on the support 1, that is, the support 1 functions to "support" the markers 2 and to make the markers 2 have a definite relative position (arrangement) relationship.

Moreover, the materials of the marker 2 and the support 1 are different, and usually the difference in density of which is large, so that in the three-dimensional image obtained by three-dimensional imaging technology (e.g. CT imaging technology), the difference in the gray scales of the marker 2 and the support 1 is large (i.e. exceeds the first predetermined value), or in other words, the marker 2 and the support 1 can be clearly distinguished in the three-dimensional image.

Specifically, the above first predetermined value can be determined according to requirements and the adopted three-dimensional imaging technology. For example, in a three-dimensional image with a total of 256 gray scales, the above first predetermined value can be 15 gray scales, 30 gray scales, 50 gray scales, or 80 gray scales, or the like.

In this case, the geometric centers of at least three markers 2 are not collinear, i.e., the total number of markers 2 is at least three, and not all the geometric centers of the markers 2 are located on a straight line. Since three points that are not collinear can define a plane, all markers 2 can define at least one plane, thereby ensuring that registration of two different coordinate systems is realized by aligning the markers.

For example, if there are only three markers 2, the geometric centers of the three markers 2 are necessarily not on a straight line. Of course, when the number of the markers 2 is four or more, there can be a situation where there are geometric centers of three markers 2 on a straight line.

Moreover, in the embodiment of the present disclosure, any two of the markers 2 are different in at least one of size and shape, that is, the two markers 2 can have the same shape and different sizes, the same size and different shapes, or different shapes and sizes. Therefore, any two of the markers 2 are distinguishable by their own shape and size.

In this case, the "shape" refers to "what" shape of the three-dimensional geometric shape of an object (e.g., spherical, ellipsoidal, cubic, tetrahedral, etc.), but without regard to the particular "dimension" of the shape. The "size" refers to a specific "dimension" of an object.

Of course, objects of the same shape can have different sizes. For example, a plurality of spheres with different diameters have the same "shapes" but have different "sizes". As such, objects with the same shape but different sizes can become the same by scaling up/down in equal proportions.

For objects with different shapes, some of their sizes can be the same. For example, the "shapes" of the spheres and hemispheres can be different, but the "sizes (diameters)" can be the same.

In this case, the different markers 2 are not in contact with each other. That is, in the three-dimensional image, the different markers 2 should be separated from each other.

Alternatively, if two objects capable of serving as markers in the optical scale are spaced with each other, they will be the two different markers 2. For example, the five black spheres in FIG. 1 are five different markers.

Figure 7:
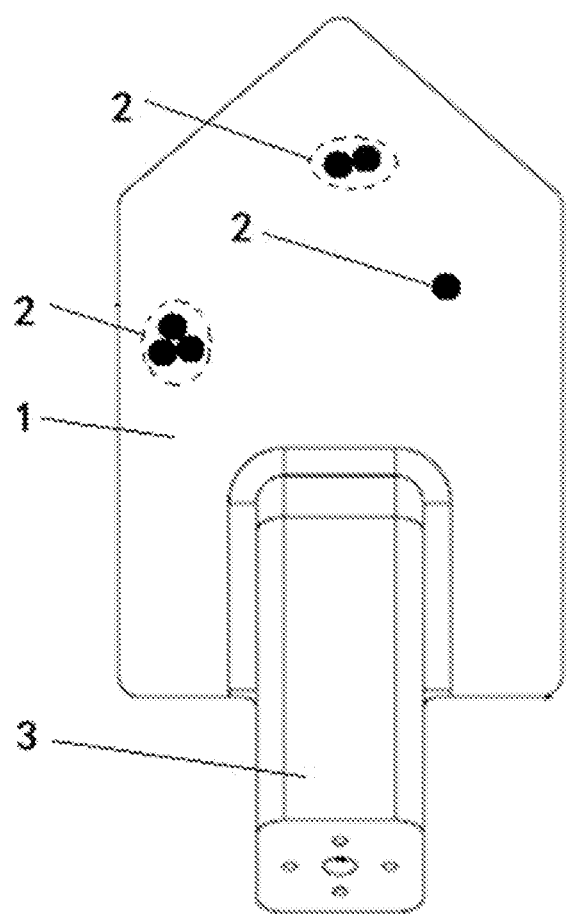
FIG. 7 is a schematic front view of another optical scale according to an embodiment of the present disclosure.

In contrast, if several objects capable of serving as markers are positioned "stacked together" and in contact with each other in the optical scale, they are one marker. For example, referring to FIG. 7, if there are six balls of the same size divided into three stacks, one stack having three balls, one stack having two balls, and the last stack having one ball, they should be considered as three markers 2, wherein one marker 2 is sphere, one marker 2 is in the form of a "string" of two balls connected together, and the other marker 2 is in the form of a stack of three balls.

In the optical scale according to the embodiment of the present disclosure, the shape and/or size of different markers 2 are different, that is, the size and/or shape of different markers 2 in the three-dimensional image are also different, so that by analyzing the size and shape of the marker 2 in the three-dimensional image, the corresponding relationship between the marker 2 in the three-dimensional image and the actual marker 2 can be identified, and the coordinate system registration between the surgical robot and the three-dimensional image (or three-dimensional imaging system) can be realized.

Therefore, the coordinate system registration of the embodiment of the present disclosure can be automatedally performed, so that it does not require manual intervention, and is simple to be operated, efficient and accurate. Moreover, in the embodiment of the present disclosure, by analyzing the shape and size of the marker 2 in the three-dimensional image, the corresponding relationship between the marker 2 in the three-dimensional image and the actual marker 2 can be determined (or the marker can be identified), without the need to analyze the position relationship (arrangement) between the markers 2, such that the required calculation process is simple, the amount of calculation is small and the time consumption is short.

In some embodiments, all of the markers 2 have the same shape, and any two of the markers 2 have different sizes.

In the three-dimensional image, it is generally simpler to identify an object when the shape of the object is determined than to identify an object when the size is determined. As such, for simplicity of operation, all markers 2 can have the same shape, but the different markers 2 can have different sizes.

In some embodiments, all of the markers 2 are spheres, and any two of the markers 2 have different diameters.

The sphere is a completely isotropic shape, which has no problem of "orientation", and one sphere can be determined by only two parameters (i.e., the center and the diameter), so that it is the simplest to identify the sphere in the three-dimensional image. Therefore, all the markers 2 can be spheres, but have different diameters.

For example, referring to FIG. 1, the diameter of the spheres of the markers 2, and the difference in diameter between the different spheres, can typically be in the order of millimeters. For example, the optical scale can comprises five spherical markers 2, each marker 2 having a diameter of 4 mm, 4.5 mm, 5 mm, 5.5 mm, 6 mm, respectively (i.e., the minimum difference in spherical diameters is 0.5 mm).

In some embodiments, there are at most two geometric centers of the markers 2 in any one line.

The embodiments of the present disclosure do not have other absolute limitations on the specific arrangement of the markers 2, as long as there are three markers 2 whose geometric centers are not collinear. However, since two points can determine a straight line, considering the requirements of coordinate system registration, it is not significant to have three or more points on a straight line, and thus, it can be specified that there is no case where the geometric centers of the three markers 2 are collinear.

In some embodiments, the geometric centers of all of the markers 2 are located in the same plane.

In this case, the requirement of the coordinate system registration can be satisfied as long as all the markers 2 can determine one plane. Therefore, considering the structural simplicity, it is preferable that the geometric centers of the markers 2 are located in the same plane.

Of course, it should be understood that the above list is only some specific examples of the distribution of the markers 2, and is not intended to limit the embodiments of the present disclosure. In practical applications, the number, shape, size, and position relationship (arrangement) the markers 2 can be selected by those skilled in the art as desired.

In some embodiments, the support 1 is a flat plate, and all the markers 2 are embedded in the flat plate.

Referring to FIG. 2, when all the markers 2 are located in the same plane, the support 1 can be a flat plate, so that each marker 2 can be embedded and fixed in the flat plate, and the structure thereof is simple and the preparation thereof is convenient.

For example, referring to FIG. 3, when the markers 2 are the above five spheres, the flat plate can have a certain thickness exceeding the maximum spherical diameter, for example, 10 mm, and the flat plate can have openings 11 with size corresponding to the diameter of the sphere of each of the above markers 2, so that each of the markers 2 can be embedded and fixed in one opening 11.

Of course, it should be understood that the above flat plate is only one specific example of the structure of the support 1, and that the support 1 can also be other forms, for example, the support 1 can comprises a plurality of support arms, each support arm having one end fixedly connected to one of the markers 2 and each support arm having one end fixedly connected to a base body.

In some embodiments, the optical scale further comprises:
a connecting structure 3 connected to the support 1 and is used for fixing the support 1 on the surgical robot.

The optical scale needs to be fixed on the surgical robot, and in order to facilitate the fixation and ensure the accuracy of the relative position of the fixed optical scale and the surgical robot, the connecting structure 3 connected to a support 1 (such as a flat plate) can be provided in the optical scale.

For example, the connecting structure 3 can refer to FIGS. 1 and 2, and is a protruding portion connected to the flat plate, and has a hole at its end for inserting a screw and connecting to a surgical robot.

Of course, it is also possible to fix the optical scale at a predetermined position of the surgical robot by means of bonding or the like, without a connecting structure.

In some embodiments, the material of the marker 2 enables that in the three-dimensional image obtained by three-dimensional imaging technology, the difference between the gray scale of the marker 2 and the gray scale of the human body exceeds a second predetermined value.

In the three-dimensional image, the human tissue of the patient is usually included as well. For this reason, the material of the marker 2 should be greatly different from the human body, so that the gray scale of the marker 2 in the three-dimensional image is greatly different from the gray scale of the human body (which refers to the maximum gray scale value that the human body tissue can reach), so that the marker 2 and the human body can be clearly distinguished.

Specifically, the above second predetermined value can be determined according to requirements and the adopted three-dimensional imaging technology. For example, in a three-dimensional image with a total of 256 gray scales, the above first predetermined value can be 30 gray scales, 50 gray scales, 80 gray scales, 100 gray scales, or 150 gray scales, or the like.

In some embodiments, the marker 2 is made of steel; the support 1 is made of plastic.

Specifically, the marker 2 can be made of steel, such as be a steel ball; and the support 1 (including connecting structure 3) can be made of plastic (e.g., transparent plastic), such as be a plastic flat plate.

The density of steel differs greatly from that of the human body and plastic, so that the marker 2 of steel is easily distinguished from the human body and the support 1. In addition, the steel and the plastic are mature materials, and which cost is low, and the preparation process is mature and simple.

Of course, the above connecting structure 3 can be formed as an integral structure with the support 1 and be made of the same material (e.g., plastic).

Figure 4:
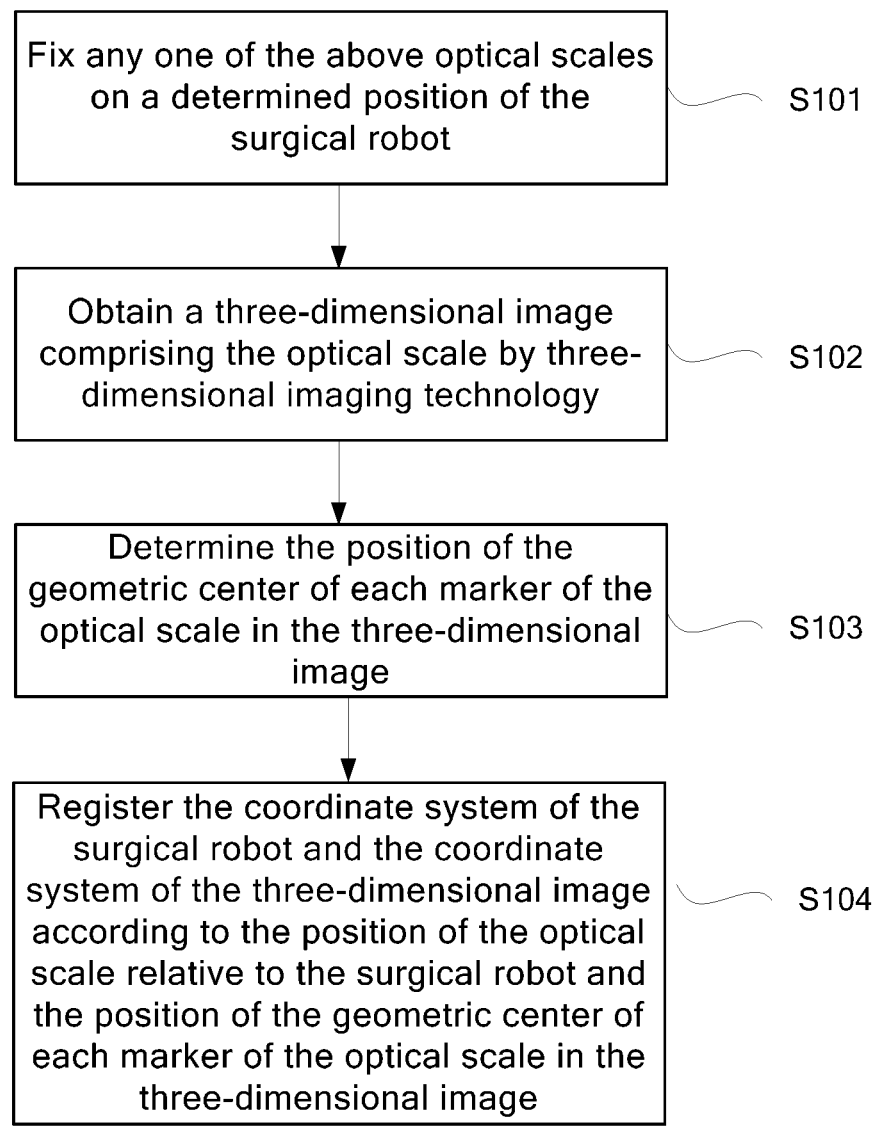
FIG. 4 is a schematic flow chart diagram of a method of coordinate system registration according to an embodiment of the present disclosure.
Figure 5:
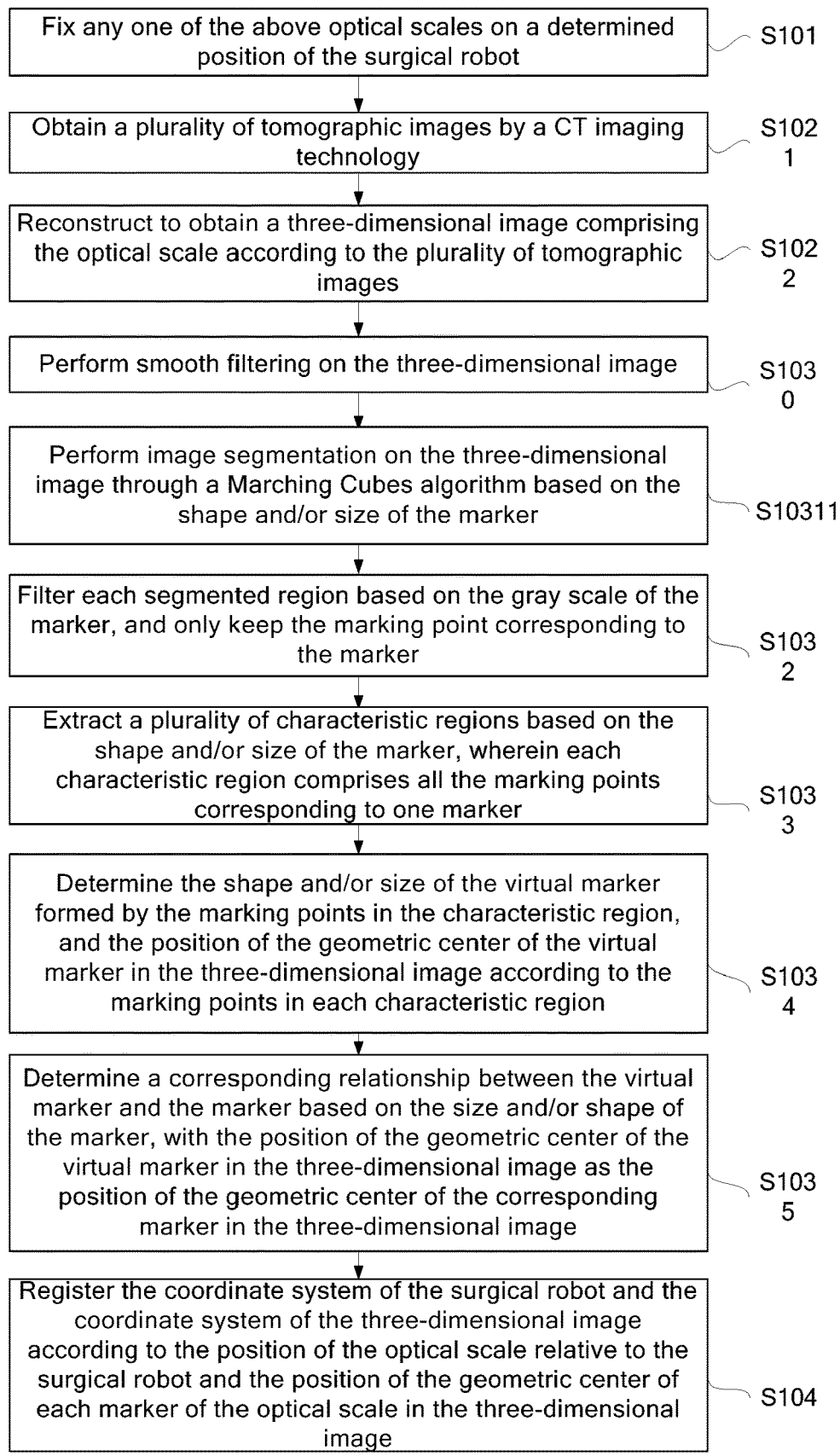
FIG. 5 is a schematic flow chart diagram of another method of coordinate system registration according to an embodiment of the present disclosure.
Figure 6:
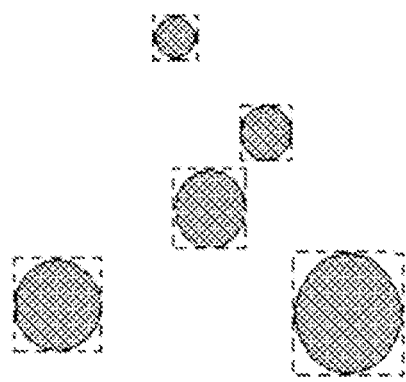
FIG. 6 is a schematic view of marking points and feature regions in a plane obtained in a method of coordinate system registration according to an embodiment of the present disclosure.

In a second aspect, referring to FIGS. 4 to 6, an embodiment of the present disclosure provides a method of coordinate system registration.

By using the above-mentioned optical scale, the method of the embodiment of the present disclosure is used for coordinate system registration, and more specifically for registering a coordinate system of a surgical robot and a coordinate system of a three-dimensional image (or a three-dimensional imaging system).

Referring to FIGS. 4 and 5, a method for coordinate system registration according to an embodiment of the present disclosure comprises the following steps:

S101, fixing any one of the above optical scales on a determined position of the surgical robot.

The above optical scale is fixed to a predetermined position of the surgical robot, for example, the optical scale is fixed to the head of the surgical robot by the above connecting structure.

Of course, since the position of each marker in the optical scale is determined, and the optical scale is also fixed at the determined position of the surgical robot, the position of each marker with respect to the surgical robot is also determined, or in other words, the position (for example, coordinate value) of each marker in the coordinate system of the surgical robot is also determined.

S102, obtaining a three-dimensional image comprising the optical scale by three-dimensional imaging technology.

That is, by means of three-dimensional imaging system, obtaining a three-dimensional image by imaging a space comprising the optical scale by using three-dimensional imaging technology, and the three-dimensional image necessarily comprises the optical scale and can also comprise other structures such as a human body and the like.

It is obvious that the three-dimensional image (or the three-dimensional imaging system) has its own coordinate system, i.e. each point in the three-dimensional image has a certain coordinate value in the coordinate system of the three-dimensional image.

In some embodiments, the three-dimensional imaging technology is a CT imaging technology.

That is, three-dimensional imaging can be performed using CT (Computed Tomography) imaging technology.

In some embodiments, the step (S102) obtaining a three-dimensional image comprising an optical scale by three-dimensional imaging technology specifically comprises:

S1021, obtaining a plurality of tomographic images by a CT imaging technology.

S1022, reconstructing to obtain a three-dimensional image comprising the optical scale according to the plurality of tomographic images.

In this case, since the CT imaging technology itself directly obtains a plurality of two-dimensional (2D) tomographic images (for example, images in DICOM format), three-dimensional reconstruction can be performed through these 2D tomographic images (that is, the content represented by each 2D image is added to a three-dimensional space) to obtain a three-dimensional image, that is, the gray scale value of each point in the three-dimensional space is determined.

S103, determining the position of the geometric center of each marker of the optical scale in the three-dimensional image.

By analyzing the three-dimensional image, identifying the markers in the three-dimensional image, and determining the position of the geometric center of each marker therein (of course, the position in the coordinate system of the three-dimensional image). Meanwhile, according to the shape and size of each marker, the corresponding relationship between the marker in the three-dimensional image and the actual marker is determined, that is, the position of the geometric center of each actual marker in the three-dimensional image is determined.

For example, assuming there are three markers A, B, C, then in the three-dimensional image, the three markers E, F, and G and the position of their respective geometric centers can necessarily also be identified; since the three markers A, B, C have different shapes and sizes, by matching the shape and size of the markers E, F, and G in the three-dimensional image with the shape and size of A, B, and C, it is possible to determine which of the three-dimensional images E, F, G corresponds to each of the three-dimensional images A, B, C.

In the embodiment of the present disclosure, the corresponding relationship of the markers can be determined by the shape and size of the markers themselves (i.e. the markers are identified), without analyzing the relative positions (arrangement) of the markers, so that the calculation process is simple, the calculation amount is small, and the time consumption is short.

S104, registering the coordinate system of the surgical robot and the coordinate system of the three-dimensional image according to the position of the optical scale relative to the surgical robot and the position of the geometric center of each marker of the optical scale in the three-dimensional image.

The position of the geometric center of each marker in the coordinate system of the three-dimensional image can be determined as described above. Also as described above, the position of each marker in the coordinate system of the surgical robot is also known.

For the same marker, its position in the coordinate system of the three-dimensional image and the position in the coordinate system of the surgical robot should obviously actually be a spatial position. Therefore, it is possible to "align" the positions of the coordinate system of the three-dimensional image and the coordinate system of the surgical robot that correspond to the same marker, and determine the relative position relationship (e.g., deviation of the origin position and deviation of each coordinate axis direction) of the coordinate system of the three-dimensional image and the coordinate system of the surgical robot in the case of such "alignment", so that the conversion of the coordinates in the two coordinate systems can be realized, that is, the "coordinate system registration" can be realized.

Obviously, since the optical scale comprises at least three non-collinear markers, the above "alignment" manner of the coordinate system of the three-dimensional image and the coordinate system of the surgical robot determined according to the embodiment of the present disclosure is unique, such that the accuracy of the coordinate system registration can be ensured.

In some embodiments, determining the position of the geometric center of each marker of the optical scale in the three-dimensional image (S103) comprises:

S1030, optionally, performing smooth filtering on the three-dimensional image.

Smooth filtering is performed on all points (including the points of the marker, the points of the support, and the points of the human body, the noise points and the like) in the three-dimensional image to eliminate the noise points, so as to facilitate the subsequent image segmentation.

In this case, generally, the more times of smooth filtering, the more conducive to image segmentation.

However, the smooth filtering also has a blurring effect, so that if the times of smooth filtering are too much, it will lead to too much blurring of the three-dimensional image. It is found that the times of smooth filtering is more appropriate around 15 times.

In this case, the specific way of the smooth filtering can be mean filtering, median filtering, Gaussian filtering, etc., and will not be described in detail herein.

S1031, performing image segmentation on the three-dimensional image based on the shape and/or size of the marker to obtain a plurality of segmented regions.

That is, segmentation parameters are set according to the shape and size (both known) of the marker, and a three-dimensional image is segmented into a plurality of "small three-dimensional images", that is, a plurality of segmented regions is obtained.

In some embodiments, the image segmentation the three-dimensional image based on the shape and/or size of the marker to obtain a plurality of segmented regions (S1031) specifically comprises:

S10311, performing image segmentation on the three-dimensional image through a Marching Cubes algorithm based on the shape and/or size of the marker.

That is, the image segmentation can be specifically performed using a marching cubes (MC) algorithm.

Specifically, the marching cubes algorithm is a "minicube" that segments the three-dimensional image into a plurality of specific sizes (the size being determined according to the shape and size of the marker). Each minicube has either no overlap with the marker, or overlaps with the marker, and by analyzing the gray scale of 8 vertices of each minicube (i.e., whether the vertices are in the marker or not), the overlap situation of each minicube with the marker (including whether and how it overlaps) can be determined, and the intersection of the iso-surface (i.e., the surface) of the marker with the 12 sides of the minicube can be determined.

S1032, filtering each segmented region based on the gray scale of the marker, and only keeping the marking point corresponding to the marker.

Filtering all points in each segmented region (small cube), specifically, filtering out points which do not belong to the markers (such as points of a human body or points of a support) according to the gray scale of the markers, so that the rest points are points (marking points) corresponding to the markers.

It should be understood that for the segmented regions not overlapping with the marker, there are no more points in the segmented regions after the current filtering, and for the segmented regions overlapping with the marker, all of the rest of the segmented regions after the current filtering are the marking points corresponding to the marker. Therefore, this step is equivalent to obtaining a "point cloud" of all markers in the three-dimensional image.

S1033, extracting a plurality of characteristic regions based on the shape and/or size of the marker, wherein each characteristic region comprises all the marking points corresponding to one marker.

That is, extraction parameters are set according to the shape and size (both known) of the marker, and three-dimensional regions with predetermined shapes but different sizes are attempted to extract the three-dimensional image, and finally, a plurality of feature regions having a predetermined shape and different sizes are extracted. In each of the above feature regions, all the marking points corresponding to one marker are included, and the marking points corresponding to the other markers are not included, and the feature region is preferably the smallest region that can "load" the marker.

For example, when the markers are the above five spheres with different diameters, the feature region can be a cube with a side length matching the diameter of the above sphere. Referring to FIG. 6, in one plane of the three-dimensional image, the marking points corresponding to the above markers can be a plurality of points within a circle in the figure, and the boundary of the feature region can be the dotted line in the figure.

S1034, determining the shape and/or size of the virtual marker formed by the marking points in the characteristic region, and the position of the geometric center of the virtual marker in the three-dimensional image according to the marking points in each characteristic region.

In each feature region, all marking points (or point clouds) belong to one marker, so that a marker (virtual marker) can be determined by these points, and the position of the geometric center of the virtual marker, as well as the size and position of the virtual marker, can be determined.

For example, when the markers are the above five spheres with different diameters, the coordinate value of the geometric center (i.e., the spherical center) of each marker can be determined by the following formula:

$$Center\_x = (\Sigma_i^n x_i)/n;$$

$$Center\_y = (\Sigma_i^n y_i)/n;$$

$$Center\_z = (\Sigma_1^n z)/n;$$

Wherein, Center_x, Center_y and Center_z are coordinate values of the center of sphere on the X axis, the Y axis and the Z axis respectively, and obviously, the X axis, the Y axis and the Z axis are three axes which are mutually vertical; $x_i$, $y_i$ and $z_i$ are the coordinates of the "i"-th marking point on the X axis, Y axis and Z axis, respectively, and n is the total number of marking points in each feature region (or the total number of marking points corresponding to the marker).

Further, the diameter of each sphere can be determined by the side length of the feature region corresponding to the sphere.

Of course, it is also feasible if the position of the virtual marker and its geometric center are determined by other means. For example, the marking points in each feature region can be "fitted" to a virtual object (virtual marker) having a predetermined shape (e.g., a sphere) by a least square method or the like, and the size and the position of the geometric center of the virtual marker can be determined.

S1035, determining a corresponding relationship between the virtual marker and the marker based on the size and/or shape of the marker, with the position of the geometric center of the virtual marker in the three-dimensional image as the position of the geometric center of the corresponding marker in the three-dimensional image.

As described above, since the shapes and sizes of the different markers are different from each other, it is possible to determine each virtual marker corresponds to which actual marker based on the shapes and sizes of the virtual markers obtained from the three-dimensional image, and it is possible to determine of the geometric center of each of the actual markers should correspond to which geometric center of the virtual marker.

For example, when the markers are the above five spheres with different diameters, the positions of the centers of the spheres (virtual markers) can be output in an order of sorting the diameters (for example, sorting from small to large), and respectively corresponds to the actual sphere (marker), that is, the position of the geometric center of each marker in the three-dimensional image is determined and used in the subsequent step of coordinate system alignment.

The present disclosure has disclosed example embodiments, and although specific terms are employed, they are used and should be interpreted in a generic and descriptive sense only and not for purposes of limitation. In some examples, it would be apparent to those skilled in the art that features, characteristics and/or elements described in connection with a particular embodiment can be used alone or in combination with features, characteristics and/or elements described in connection with other embodiments, unless expressly stated otherwise. Therefore, it will be understood by those skilled in the art that various changes in form and details can be made therein without departing from the scope of the disclosure as set forth in the appended claims.

What is claimed is:

1. An optical scale comprising a support and at least three markers, wherein,
    the markers are fixed on the support; among all the markers, there are at least three markers whose geometric centers are not collinear; any two of the markers are different in at least one of size and shape, and any different markers do not contact each other;
    the material of the markers and the support enables that in a three-dimensional image obtained by three-dimensional imaging technology, the difference between a gray scale of the markers and a gray scale of the support exceeds a first predetermined value; and
    there are at most two geometric centers of the markers in any one line.

2. The optical scale according to claim 1, wherein,
    all of the markers have the same shape, and any two of the markers have different sizes.

3. The optical scale according to claim 2, wherein,
    all of the markers are spherical, and any two of the markers have different diameters.

4. The optical scale according to claim 1, wherein,
    the geometric centers of all of the markers are located in the same plane.

5. The optical scale according to claim 4, wherein,
    the support is a flat plate, and all the markers are embedded in the flat plate.

6. The optical scale according to claim 1, wherein, further comprising:
    a connecting structure connected to the support and is used for fixing the support on a surgical robot.

7. The optical scale according to claim 1, wherein,
    the material of the markers enables that in a three-dimensional image obtained by three-dimensional imaging technology, the difference between a gray scale of the markers and a gray scale of human body exceeds a second predetermined value.

8. The optical scale according to claim 1, wherein,
    the markers are made of steel; and
    the support is made of plastic.

9. A method of coordinate system registration, comprising:
    fixing an optical scale on a determined position of a surgical robot, wherein the optical scale is the optical scale according to claim 1;
    obtaining a three-dimensional image comprising the optical scale by three-dimensional imaging technology;
    determining the position of the geometric center of each marker of the optical scale in the three-dimensional image;
    registering the coordinate system of the surgical robot and the coordinate system of the three-dimensional image according to the position of the optical scale relative to the surgical robot and the position of the geometric center of each marker of the optical scale in the three-dimensional image.

10. The method of claim 9, wherein,
    the three-dimensional imaging technology is a CT imaging technology.

11. The method of claim 10, wherein, the step that obtaining a three-dimensional image comprising the optical scale by three-dimensional imaging technology comprising:
    obtaining a plurality of tomographic images by CT imaging technology;
    reconstructing to obtain a three-dimensional image comprising the optical scale according to the plurality of tomographic images.

12. The method of claim 9, wherein, the step that determining the position of the geometric center of each marker of the optical scale in the three-dimensional image comprising:
    performing image segmentation on the three-dimensional image based on the shape and/or size of the marker to obtain a plurality of segmented regions;
    filtering each of the segmented regions based on the gray scale of the marker, and only keeping the marking points corresponding to the marker;
    extracting a plurality of characteristic regions based on the shape and/or size of the marker, wherein each characteristic region comprises all the marking points corresponding to one marker;
    determining the shape and/or size of the virtual marker formed by the marking points in each characteristic region, and the position of the geometric center of the virtual marker in the three-dimensional image according to the marking points in each characteristic region;
    determining a corresponding relationship between the virtual marker and the marker based on the size and/or shape of the marker, with the position of the geometric center of the virtual marker in the three-dimensional image as the position of the geometric center of the corresponding marker in the three-dimensional image.

13. The method of claim 12, wherein, the step that performing image segmentation on the three-dimensional image based on the shape and/or size of the marker to obtain a plurality of segmented regions comprising:
    performing image segmentation on the three-dimensional image through a Marching Cubes algorithm based on the shape and/or size of the marker.

* * * * *